(12) United States Patent
Taniguchi

(10) Patent No.: US 10,006,842 B2
(45) Date of Patent: Jun. 26, 2018

(54) METHOD FOR PRODUCING CELL CONCENTRATE

(71) Applicant: KANEKA CORPORATION, Kita-ku (JP)

(72) Inventor: Shuhei Taniguchi, Settsu (JP)

(73) Assignee: KANEKA CORPORATION, Kita-ku (JP)

( * ) Notice: Subject to any disclaimer, the term of this patent is extended or adjusted under 35 U.S.C. 154(b) by 566 days.

(21) Appl. No.: 14/424,574

(22) PCT Filed: Aug. 19, 2013

(86) PCT No.: PCT/JP2013/072056
§ 371 (c)(1),
(2) Date: Feb. 27, 2015

(87) PCT Pub. No.: WO2014/034456
PCT Pub. Date: Mar. 6, 2014

(65) Prior Publication Data
US 2015/0204767 A1    Jul. 23, 2015

(30) Foreign Application Priority Data
Aug. 30, 2012 (JP) .................. 2012-190207

(51) Int. Cl.
*G01N 1/40* (2006.01)
*B01D 69/02* (2006.01)
(Continued)

(52) U.S. Cl.
CPC ........... *G01N 1/4077* (2013.01); *B01D 61/18* (2013.01); *B01D 63/02* (2013.01); *B01D 69/02* (2013.01);
(Continued)

(58) Field of Classification Search
CPC ...... A01N 1/0284; B01D 63/02; B01D 71/26; B01D 71/68; B01D 2323/02;
(Continued)

(56) References Cited

U.S. PATENT DOCUMENTS 3,852,155 A    12/1974    Moore
6,010,627 A    1/2000    Hood, III
(Continued)

FOREIGN PATENT DOCUMENTS

CN    1231212 A    10/1999
EP    1 673 857 A1    7/2006
(Continued)

OTHER PUBLICATIONS

Flow Rate Calculator (2010). Internet article, 1 page.*
(Continued)

*Primary Examiner* — Sean C. Barron
(74) *Attorney, Agent, or Firm* — Oblon, McClelland, Maier & Neustadt, L.L.P.

(57) ABSTRACT

Provided is a simple method for producing a cell concentrate (other than human blood) in a short time with neither loss of cells nor an excessive burden on cells. Included is a method for producing a cell concentrate using an inside-out filtration system for processing a cell suspension, the system including: a cell suspension inlet port; a filtrate outlet port; a cell suspension outlet port; and hollow fiber separation membranes provided between the cell suspension inlet port and the cell suspension outlet port, wherein the membranes have a total cross-sectional area of 0.5-1.5 cm$^2$, the membranes have an inside membrane area of 0.2 m$^2$ or less, the suspension is flowed inside the membranes at a linear velocity of 500-1200 cm/min, and the quotient of the division of the initial filtrate flow rate from the filtrate outlet port by the flow rate into the cell suspension inlet port is 0.4-0.7.

10 Claims, 1 Drawing Sheet

(51) Int. Cl.
*B01D 69/08* (2006.01)
*C12N 1/04* (2006.01)
*C12M 1/00* (2006.01)
*B01D 71/26* (2006.01)
*B01D 71/18* (2006.01)
*B01D 71/68* (2006.01)
*B01D 71/10* (2006.01)
*B01D 63/02* (2006.01)
*C12M 1/12* (2006.01)
*B01D 61/18* (2006.01)

(52) U.S. Cl.
CPC ........... *B01D 69/081* (2013.01); *B01D 71/10* (2013.01); *B01D 71/26* (2013.01); *B01D 71/68* (2013.01); *C12M 47/02* (2013.01); *C12N 1/04* (2013.01); *C12M 25/10* (2013.01); *G01N 2001/4088* (2013.01)

(58) Field of Classification Search
CPC ........ B01D 2325/20; C12N 1/02; C12N 1/04; C12N 5/06
See application file for complete search history.

(56) References Cited

U.S. PATENT DOCUMENTS

| | | | | |
|---|---|---|---|---|
| 8,051,991 | B2 * | 11/2011 | Krause | B01D 67/0011 210/500.23 |
| 2013/0280767 | A1 | 10/2013 | Kobayashi et al. | |
| 2014/0287502 | A1 | 9/2014 | Taniguchi | |

FOREIGN PATENT DOCUMENTS

| | | |
|---|---|---|
| EP | 2 335 814 A1 | 6/2011 |
| JP | 63-160578 A | 7/1988 |
| JP | 06-098758 A | 4/1994 |
| JP | 2928913 B2 | 5/1999 |
| JP | 2928913 B2 | 8/1999 |
| JP | 2003-319774 A | 11/2003 |
| JP | 2005-336080 A | 12/2005 |
| JP | 2006-129987 A | 5/2006 |
| JP | 2006-305333 A | 11/2006 |
| JP | 2007-524396 A | 8/2007 |
| JP | 2008-229612 | 10/2008 |
| WO | WO 2004/004873 A1 | 1/2004 |
| WO | WO 2011/091248 A1 | 7/2011 |
| WO | WO 2011/091248 A8 | 7/2011 |
| WO | WO 2012/090863 A1 | 7/2012 |
| WO | WO 2013/061859 A1 | 5/2013 |

OTHER PUBLICATIONS

International Search Report dated Nov. 5, 2013 in PCT/JP2013/072056.
International Preliminary Report on Patentability and Written Opinion dated Mar. 3, 2015 in PCT/JP2013/072056.
F. Castino, et al., "Washing frozen red blood cell concentrates using hollow fibres" Journal of Membrane Science, vol. 110, 1996, pp. 169-180.
English translation of the International Preliminary Report on Patentability dated May 8, 2014 in PCT/JP2012/076964.
English translation of the Written Opinion dated Dec. 25, 2012 in PCT/JP2012/076964.
International Search Report dated Dec. 25, 2012 in PCT/JP2012/076964.
Loc Trinh, et al., "Recovery of insect cells using hollow fiber microfiltration", Biotechnology and Bioengineering, vol. 48, No. 4 Nov. 20, 1995, pp. 401-405.
Joseph Shiloach, et al., "Hollow fiber microfiltration methods for recovery of rat basophilic leukemia cells (RBL-2H3) from tissue culture media", Biotechnology Progress, vol. 2, No. 4, Dec. 1986, pp. 230-233.
S. A. Weiss, et al., "Improved Method for the Production of Insect Cell Cultures in Large Volume" In Vitro, vol. 17, No. Jun. 1981, pp. 495-502.

* cited by examiner

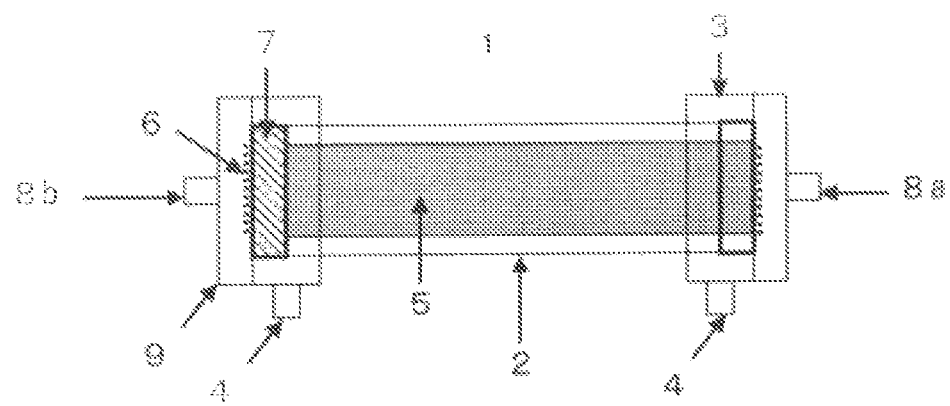

METHOD FOR PRODUCING CELL CONCENTRATE

TECHNICAL FIELD

The present invention relates to techniques for producing cell concentrates using cell suspension processing systems packed with hollow fiber separation membranes.

BACKGROUND ART

Cell therapy employs a technique in which cells from a living donor are implanted into a patient either directly or after being cultured in vitro. Cells for use in such treatment are suspended in a solution suitable for the treatment, or adjusted to a suitable concentration prior to implantation. Unfortunately, cells may not be obtained from a living donor at a sufficient cell concentration for treatment. Moreover, in vitro cultures of cells taken from a living donor often contain unnecessary tissue-derived components, culture media, and the like. Accordingly, the following processes are necessary prior to using cells taken from a living donor or cultured cells for treatment: removing unnecessary components and media, suspending (washing) the cells in a solution or other media suitable for the treatment, and concentrating the cells to a level suitable for the treatment.

To achieve this goal, concentration and washing processes using centrifugation have been used. For example, a technique of separating and concentrating regenerative cells from human tissues by centrifugation is disclosed (Patent Literature 1). Unfortunately, such processes using centrifugation can be implemented in a limited number of facilities because of the necessity of a large-scale device, a burden on cells, and increased costs. Another problem is that when the supernatant of a cell suspension obtained after the cells are sedimented by centrifugation is removed for washing, the cells may be exposed to atmospheric air, which may cause contamination, for example.

To solve this problem, it has been proposed to separate and filter a cell suspension using hollow fiber separation membranes, which are compact and simple devices (Patent Literature 2). For use in concentrating a cell suspension for cell therapy, hollow fiber separation membranes with large pore sizes are thought to be suitable because the concentration process should be carried out in a short time to reduce damage to cells and also because unnecessary components and medium components have high molecular weights. Unfortunately, hollow fiber separation membranes with large pore sizes may cause clogging with cells, and the like, or may allow more cells to adhere to the hollow fiber separation membranes, resulting in a reduced number of cells in the process of preparing the concentrate.

CITATION LIST

Patent Literature

Patent Literature 1: JP 2007-524396 T
Patent Literature 2: JP 2928913 B

SUMMARY OF INVENTION

Technical Problem

An object of the present invention is to solve the above problems in the preparation of cell concentrates using hollow fiber separation membranes. Specifically, the present invention provides a method for producing a cell concentrate which can concentrate cell suspensions in a short time while maintaining high cell recovery rates even though hollow fiber separation membranes with large pore sizes are used. The present invention further provides a method for producing a cell concentrate which can efficiently remove unnecessary components, such as proteins, in suspensions.

Solution to Problem

The Intensive studies to solve the above problems by the present inventor have revealed that cell concentrates can be prepared in a short time while maintaining high cell recovery rates even though hollow fiber separation membranes with large pore sizes are used, as long as filtrate flow rate and linear velocity are controlled within specific ranges. This has led to the completion of the present invention.

Specifically, the present invention relates to a method for producing a cell concentrate using an inside-out filtration system for processing a cell suspension, the system including: a cell suspension inlet port; a filtrate outlet port; a cell suspension outlet port; and a set of hollow fiber separation membranes provided between the cell suspension inlet port and the cell suspension outlet port, wherein the hollow fiber separation membranes have a total cross-sectional area of 0.5 cm$^2$ to 1.5 cm$^2$, the hollow fiber separation membranes have an inside membrane area of 0.2 m$^2$ or less, the cell suspension is flowed inside the hollow fiber separation membranes at a linear velocity of 500 cm/min to 1200 cm/min, and the quotient of the division of an initial filtrate flow rate from the filtrate outlet port by a flow rate into the cell suspension inlet port is 0.4 to 0.7.

The hollow fiber separation membranes preferably have an inner diameter of 300 μm to 1000 μm.

The hollow fiber separation membranes preferably have an average pore size of 0.1 μm or more.

The hollow fiber separation membranes are preferably made of a polysulfone-, polyolefin-, or cellulose-based material.

The hollow fiber separation membranes are preferably made of polyethersulfone.

The cell suspension is preferably an immune cell suspension.

The present invention further relates to a method for producing a cell concentrate, which includes the steps of: washing a cell concentrate obtained by the above production method by repeating dilution with a liquid free from cells and concentration; and further concentrating the resulting concentrate.

The present invention further relates to a method for cryopreserving cells, which includes the step of cryopreserving a cell concentrate obtained by any one of the above production methods with liquid nitrogen.

Advantageous Effects of Invention

According to the present invention, cell concentrates can be prepared in a short time while maintaining high cell recovery rates even though hollow fiber separation membranes with large pore sizes are used to concentrate cell suspensions. Further, since the present invention allows for efficient removal of unnecessary components, such as proteins, in suspensions, and also allows for processing in an aseptic closed system, cell concentrates prepared by the methods of the present invention are usable for cell therapy.

BRIEF DESCRIPTION OF DRAWINGS

FIG. 1 illustrates a cell suspension processing system used in Examples.

DESCRIPTION OF EMBODIMENTS

The following description is offered to illustrate the present invention.

FIG. 1 illustrates a non-limiting example of a cell suspension processing system in the present invention. A tubular housing 1 consists of a straight body 2, and heads 3 and headers 9, which are provided on the ends of the body. The head 3 is provided with a filtrate outlet port 4. The filtrate outlet port may be provided on one end or both ends. In this shown example, the headers 9 are respectively provided with a cell suspension inlet port 8a and a cell suspension outlet port 8b. The tubular housing 1 includes, inside the housing, a hollow fiber separation membrane bundle 5 packed therein, and resin layers 7 in the headers 9, which immobilize the hollow fiber separation membrane bundle 5 inside the housing and form open ends 6 of the hollow fiber separation membranes, as well as their equivalent structures in the heads 3. The resin layers 7 and the open ends 6 are configured to be capped with the headers 9 (or the heads 3), and the cell suspension inlet and outlet ports 8a and 8b are configured to be separated from the filtrate outlet ports 4 by a wall member, which is a part of the hollow fiber separation membranes, so that the cell suspension inlet and outlet ports 8a and 8b are discontinuous with the filtrate outlet ports 4.

In the example shown in FIG. 1, these parts are distinguished from each other for convenience as follows: the body 2, heads 3, headers 9, and other parts of the tubular housing. If the header 9 is designed to be integrated with the head 3 of the tubular housing, or if the body 2 and the heads 3 of the tubular housing are separate components, the tubular housing may have any structure, provided that the cell suspension inlet port and the cell suspension outlet port are not separated by the wall member which is a part of the hollow fiber separation membranes, so that they are continuous, and that the cell suspension inlet and outlet ports are separated from the filtrate outlet ports by the wall member which is a part of the hollow fiber separation membranes.

The tubular housing of the cell suspension processing system in the present invention is preferably packed with a bundle consisting of approximately several tens to several thousands of hollow fiber separation membranes. In the present invention, the hollow fiber separation membranes may be arranged in a linear, curved or spiral configuration, and the hollow fiber separation membranes may have any configuration, without limitation, provided that both the ends of the hollow fiber separation membranes are held between the cell suspension inlet port and the cell suspension outlet port.

Examples of materials for the tubular housing of the cell suspension processing system include acrylonitrile polymers, such as acrylonitrile-butadiene-styrene terpolymer; halogenated polymers, such as polytetrafluoroethylene, polychlorotrifluoroethylene, tetrafluoroethylene-hexafluoropropylene copolymer, or polyvinyl chloride; and polyamide, polyimide, polysulfone, polycarbonate, polyethylene, polypropylene, polyvinylchloride acrylic copolymers, acrylonitrile, butadiene-styrene, polystyrene, and polymethylpentene. In particular, sterilization-resistant materials, including specifically polypropylene, polyvinyl chloride, polyethylene, polyimide, polycarbonate, polysulfone, polymethylpentene, and polystyrene, are preferred.

Preferred examples of materials for the resin layers for immobilizing the hollow fiber separation membranes include common adhesive materials such as polyurethane resins, epoxy resins, and silicon resins.

The "inside-out filtration" mode herein means that a filtrate substantially free from cells is filtered from the inside to the outside of hollow fiber separation membranes. The expression "filtrate substantially free from cells" herein means that the number of cells present in the filtrate does not exceed 0.1% of the number of cells in the cell suspension before introduction. For example, the cell suspension introduced through the cell suspension inlet port may be filtered to remove a filtrate under water pressure applied when the cell suspension flows into the inside of the hollow fiber separation membrane bundle in the cell suspension processing system, or, alternatively, negative pressure may be applied outside the hollow fiber separation membranes to allow a filtrate to be removed towards the outside.

As used herein, the term "total cross-sectional area" of the hollow fiber separation membranes refers to the total of the cross-sectional areas of the lumens of the hollow fiber separation membranes in the cell suspension processing system, and the total cross-sectional area can be determined by the formula: (Total cross-sectional area)=(Number of fibers)×π×(Hollow fiber inner diameter)×(Hollow fiber inner diameter)/4. The total cross-sectional area of the hollow fiber separation membranes in the present invention is at least 0.5 cm$^2$ but not more than 1.5 cm$^2$, and is preferably at least 0.6 cm$^2$ but not more than 1.5 cm$^2$, more preferably at least 0.75 cm$^2$ but not more than 1.5 cm$^2$, and still more preferably at least 0.75 cm$^2$ but not more than 1.25 cm$^2$. If the total cross-sectional area is less than 0.5 cm$^2$, a sufficient inside membrane area for processing a cell suspension cannot be ensured and thus the processing tends to take a long time. Also, if the total cross-sectional area is more than 1.5 cm$^2$, the cell suspension introduced into the cell suspension processing system tends to be dispersed instead of flowing into the hollow fibers, thereby resulting in reduced filtration efficiency.

As used herein, the term "inside membrane area" of the hollow fiber separation membranes refers to the total of the inside areas of the hollow fiber separation membranes in the cell suspension processing system, and the inside membrane area can be determined by the formula: (Inside membrane area)=(Number of fibers)×π×(Hollow fiber inner diameter)×(Effective length). The term "effective length" used herein refers to a portion of the entire length of the hollow fiber separation membranes provided between the inlet and outlet of the cell suspension processing system, through which liquid passes. The inside membrane area of the hollow fiber separation membranes in the present invention is 0.2 m$^2$ or less, and is preferably 0.18 m$^2$ or less, and more preferably 0.15 m$^2$ or less. The inside membrane area of the hollow fiber separation membranes in the present invention is also preferably 0.05 m$^2$ or more. If the inside membrane area is more than 0.2 m$^2$, more cell suspension tends to remain in the hollow fiber separation membranes, thereby resulting in reduced recovery. Conversely, if the inside membrane area is less than 0.05 m$^2$, then filtrate flow rate tends not to be sufficient to carry out the processing in a short time.

In the present invention, the flow rate of the cell suspension into the cell suspension inlet port is not particularly limited, as long as it does not decrease recovery and viability. The flow rate is preferably at least 200 mL/min but not more than 1000 mL/min, and more preferably at least 300 mL/min but not more than 800 mL/min. If the flow rate is less than 200 mL/min, filtrate flow rate cannot be set to a high level, which tends to prevent efficient concentration. Also, if the flow rate is more than 1000 mL/min, then higher pressure needs to be applied to the cell suspension by a pump to deliver the cell suspension, and thus the cell suspension may apply strong shear and pressure to cells and damage them during the flowing through the lines and hollow fibers. This may eventually decrease recovery and viability.

The term "linear velocity" used herein is defined as the quotient of the division of the amount of fluid flowing into the lumens of the hollow fiber separation membranes per unit time by the total cross-sectional area of the hollow fiber separation membranes. In the present invention, the linear velocity of the cell suspension flowing inside the hollow fiber separation membranes is at least 500 cm/min but not more than 1200 cm/min, and is preferably at least 500 cm/min but not more than 1000 cm/min. If the linear velocity is less than 500 cm/min, more cells tend to adhere to the surface of the hollow fiber membranes, thereby resulting in reduced recovery. If the linear velocity is more than 1200 cm/min, then high shear stress is applied to cells and thus the cells tend to be damaged.

The term "initial filtrate flow rate" used herein refers to the filtrate flow rate per unit time used to filter an initial 500 mL filtrate at the beginning of the treatment. The initial filtrate flow rate is not particularly limited, as long as it does not decrease recovery and viability. The initial filtrate flow rate is preferably at least 50 mL/min but not more than 600 mL/min, and more preferably at least 100 mL/min but not more than 400 mL/min. If the flow rate is less than 50 mL/min, the concentration process takes a long time, which tends to prevent efficient concentration. Also, if the flow rate is more than 600 mL/min, cells tend to be stuck to the membrane surface and damaged.

In the present invention, the quotient of the division of the initial filtrate flow rate by the flow rate into the cell suspension inlet port is at least 0.4 but not more than 0.7, and is preferably at least 0.4 but not more than 0.6. If the quotient is less than 0.4, the flow of the cell suspension tends to become irregular so that cells adhere to the hollow fiber membranes, thereby resulting in reduced recovery. Conversely, if the quotient is more than 0.7, the cell concentration of the cell suspension in the hollow fibers is rapidly excessively increased, which tends to allow cells to adhere to the hollow fiber membranes, resulting in reduced recovery.

In the present invention, the inner diameter of the hollow fiber separation membranes is preferably at least 300 µm but not more than 1000 µm, and more preferably at least 400 µm but not more than 800 µm. If the inner diameter is less than 300 µm, cells tend to be exposed to high shear stress and therefore to be damaged, while if the inner diameter is more than 1000 µm, the specific surface with which the cell suspension comes into contact becomes so small that filtration tends not to be efficiently performable.

The average pore size of the hollow fiber separation membranes is preferably 0.1 µm or more, and more preferably 0.2 µm or more. The average pore size of the inside pores of the hollow fiber separation membranes is preferably 1 µm or less. If the average pore size is less than 0.1 µm, the filtrate flow rate obtained tends not to be high, or unnecessary components such as proteins tend not to be efficiently removable. Conversely, if the average pore size is more than 1 µm, then some pores present on the hollow fiber separation membranes have a pore size similar to the size of cells, which tends to cause the pores to be clogged with cells, thereby greatly reducing cell recovery.

Preferred resin materials for the hollow fiber separation membranes used in the present invention are synthetic polymer materials, for material safety and stability reasons, and the like. More preferred are polysulfone-, polyolefin-, or cellulose-based polymer materials. For material safety, stability, and availability reasons, polyethersulfone, polyethylene, and cellulose esters are most preferred.

Examples of cells that can be concentrated by the production method of the present invention include living pluripotent stem cells such as induced pluripotent stem cells (iPS cells), embryonic stem cells (ES cells), mesenchymal stem cells, adipose-derived mesenchymal cells, adipose-derived stromal stem cells, pluripotent adult stem cells, bone marrow stroma cells, and hematopoietic stem cells; lymphoid cells such as T cells, B cells, killer T cells (cytotoxic T cells), NK cells, NKT cells, and regulatory T cells; macrophages, monocytes, dendritic cells, granulocytes, red blood cells, and platelets; somatic cells such as nerve cells, muscle cells, fibroblasts, liver cells, and myocardial cells; and cells subjected to gene transfer, differentiation or other treatments.

Preferred among these are immune cells such as granulocytes, T cells, B cells, killer T cells (cytotoxic T cells), NK cells, NKT cells, regulatory T cells, macrophages, and dendritic cells.

Moreover, the cell suspension used in the present invention may be any suspension containing cells, without limitation, and examples thereof include suspensions obtained from living tissues, such as fat, skin, blood vessels, cornea, oral cavity, kidney, liver, pancreas, heart, nerve, muscle, prostate, intestines, amnion, placenta, or umbilical cord, through treatment, such as enzymatic treatment, disruption, extraction, decomposition, and/or ultrasonic treatment. Other examples include cell suspensions prepared from blood or bone marrow through pre-treatment, such as density gradient centrifugation, filtration, enzymatic treatment, decomposition, and/or ultrasonic treatment. Further examples include cell suspensions obtained by culturing such cells as described above, in vitro using a culture medium. Examples of the culture media include DMEM, α-MEM, MEM, IMEM, RPMI-1640, and culture media containing a stimulation factor, such as cytokines, antibodies or peptides, or the like.

The cell concentrates prepared by the present invention may be further washed. The "washing" means to replace a biological fluid, medium, or others in which cells are suspended with a washing solution. This removes unnecessary components in the concentrate and thus allows the cell concentrates to be suitably used in implantation into to humans or animals. The cell concentrates may be repeatedly washed.

The washing solution is a liquid free from cells, and examples include physiological saline, infusion solutions, media, distilled water, inorganic salts, saccharides, serum, protein-containing liquids, buffers, media, and plasma. Physiological saline and infusion solutions are preferred from a safety standpoint.

Moreover, the cell concentrates prepared by the method of the present invention can be used for, but not limited to, the treatment of leukemia, regeneration of the heart muscle or blood vessels, diseases such as stem cell deficiency, bone diseases, cartilage diseases, ischemic diseases, blood vascular diseases, neuropathies, burns, chronic inflammation, cardiac diseases, immunodeficiencies, and Crohn's disease, tissue engineering, including breast implantation, wrinkle reduction, cosmetic surgery, and tissue augmentation to treat tissue depression; immunotherapies, including T cell therapy, NKT cell therapy, and dendritic cell transfer therapy; gene therapies using gene-transferred cells, and other applications. Also, concentrated cells may be seeded on a structure such as a scaffold prior to use in therapy.

The cell concentrates prepared by the method of the present invention may be further cultured. By replacing the liquid in the cell concentrate obtained after washing with a medium, and culturing the cells, the following can be achieved, for example: increase in the number of cells; differentiation of the cells; transformation of the cells; and gene transfer. Examples of the media that can be used to grow the cells include DMEM, α-MEM, MEM, IMEM, and RPMI-1640. For example, stimulation factors, such as cytokines, antibodies or peptides, may also be used in the culture.

The cell concentrates prepared by the method of the present invention can be prepared into pharmaceutical compositions. Such pharmaceutical compositions can be prepared by mixing the concentrated cells with pharmaceutically acceptable additives. Examples of the pharmaceutically acceptable additives include anticoagulants, nutritional sources (e.g. vitamins), and antibiotics.

The cell concentrates prepared by the method of the present invention may be further cryopreserved. Liquid nitrogen is preferably used in the cryopreservation because it causes less damage to cells. Moreover, cryopreserved cells may be thawed prior to use in implantation into humans or animals or in studies, or may be thawed to culture them again. Since the cells in the cell concentrates prepared by the method of the present invention are less damaged by the concentration process, they can be suitably used after being cryopreserved and/or thawed or in other applications.

The following illustrates an example of the method for producing a cell concentrate of the present invention, but the present invention is not limited only to this example. Various modifications are possible without departing from the spirit of the present invention.

In the method for producing a cell concentrate from a cell suspension using a cell suspension processing system, a cell suspension is introduced into the hollow fiber separation membranes in the cell suspension processing system, and filtered from the inside out to remove a filtrate substantially free from cells towards the outside of the hollow fiber separation membranes, and a cell component-enriched cell suspension is then discharged from the cell suspension outlet port. The term "filtrate substantially free from cells" herein means that the number of cells present in the filtrate does not exceed 0.1% of the number of cells in the cell suspension before introduction.

First, tubes or the like are attached to the cell suspension inlet and outlet ports of the cell suspension processing system (such tubes partially constitute lines through which a cell suspension flows into and out of the hollow fibers in the processing system), and further connected to a container (e.g. a cell bag) containing a cell suspension so that the cell suspension can circulate between the bag or the like container and the cell suspension processing system. In order to circulate the suspension, a machine, such as a pump, may be contemplated to be placed in the lines. Moreover, tubes connected to a waste tank or the like are preferably connected to the filtrate outlet ports. In this case, the entire lines are preferably installed in an aseptic environment. Moreover, in this case, pressure may be applied to the separation membranes, for example, by narrowing the flow path on the cell suspension outlet port side, or filtration may be carried out while applying pressure to the tube on the filtration side using a pump or the like. Thus, various filtration techniques generally used with hollow fiber separation membranes can be used in combination.

After the concentration process has progressed, a washing solution (e.g. a buffer) may be added, and the concentration process may then be repeated to wash cells or replace the medium. At this time, the washing solution is introduced from an inlet port placed in the circulation line tube, preferably from an inlet port through which the solution can be aseptically injected.

The concentrated and washed cell suspension can be collected in a recovery bag or the like and then used in applications such as treatment. In this case, the collection in a recovery bag is preferably carried out in an aseptic manner using an additional outlet port (e.g. a three-way stopcock) placed in the circulation line tube.

The cell suspension processing system in the present invention may be sterilized before use. The sterilization may be carried out by any method without limitation, and general sterilization methods for medical devices such as γ-ray sterilization, electron beam sterilization, EOG sterilization, and high-pressure steam sterilization can be suitably used.

EXAMPLES

The following shows experimental results to illustrate the present invention. The "cell recovery rate" used herein refers to the quotient of the division of the number of cells in a cell suspension concentrated to a certain degree by the number of cells in the cell suspension before processing. A higher quotient indicates better recovery efficiency. In the examples below, cell concentration was defined as the cell concentration in the white blood cell fraction in a cell suspension, as measured with a blood cell counter (Sysmex Corp., K-4500). The number of cells was calculated from the amount of a cell suspension and the cell concentration. The filtration time (s) taken from the start of the processing to the end of the filtration of 1000 mL of medium was also measured. The cell suspension to be processed was 1500 mL of a cultured Jurkat cell suspension (10% FBS-containing RPMI 1640 medium).

In the examples, vinyl chloride tubes were connected to the inlet and outlet ports of the cell suspension processing system. A cell suspension was retained in a plastic container, and the free ends of the vinyl chloride tubes respectively extending from the ends of the cell suspension processing system were lowered to be immersed in the suspension so that the suspension can circulate through the module and tubes. A pump was placed in the vinyl chloride tube to appropriately set the velocity of the suspension flow. Additional tubes were attached to the filtrate outlet ports of the cell suspension processing system and arranged to discharge a filtrate into a waste container. The cell suspension was filtered while circulating the suspension through the lines at a velocity controlled by the pump. After the cell suspension was concentrated to a certain amount (100 mL to 150 mL), the cell suspension remaining in the tubes and the hollow fiber separation membranes was flushed out with air, the pump was turned off, and the number of cells present in the cell suspension in the plastic container was determined to calculate recovery rate.

Example 1

A cell suspension processing system was prepared using 250 hollow fiber separation membranes made of polyethersulfone [hollow fiber inner diameter: 570 μm, pore size: 0.2

μm]. The prepared processing system had an inside membrane area of 0.1 m$^2$, and a total cross-sectional area of the hollow fiber separation membranes of 0.637 cm$^2$. The cell suspension was passed through the system under the following conditions: flow rate into cell suspension inlet port: 460 mL/min (linear velocity: 722 cm/min); and initial filtrate flow rate from filtrate outlet port: 285 mL/min. The cell recovery rate and filtration time thus determined were 88% and 190 s, respectively.

Example 2

The same separation membranes as those used in Example 1 were used. The number of hollow fibers used was 300, and the prepared processing system had an inside membrane area of 0.12 m$^2$, and a total cross-sectional area of the hollow fiber separation membranes of 0.765 cm$^2$. The cell suspension was passed through the system under the following conditions: flow rate into cell suspension inlet port: 420 mL/min (linear velocity: 549 cm/min); and initial filtrate flow rate from filtrate outlet port: 200 mL/min. The cell recovery rate and filtration time thus determined were 84% and 290 s, respectively.

Example 3

The same cell suspension processing system as that of Example 2 was prepared. The cell suspension was passed through the system under the following conditions: flow rate into cell suspension inlet port: 640 mL/min (linear velocity: 837 cm/min); and initial filtrate flow rate from filtrate outlet port: 301 mL/min. The cell recovery rate and filtration time thus determined were 100% and 210 s, respectively.

Example 4

The same separation membranes as those used in Example 1 were used. The number of hollow fibers used was 450, and the prepared processing system had an inside membrane area of 0.19 m$^2$, and a total cross-sectional area of the hollow fiber separation membranes of 1.147 cm$^2$. The cell suspension was passed through the system under the following conditions: flow rate into cell suspension inlet port: 660 mL/min (linear velocity: 575 cm/min); and initial filtrate flow rate from filtrate outlet port: 273 mL/min. The cell recovery rate and filtration time thus determined were 99% and 200 s, respectively.

Comparative Example 1

The same cell suspension processing system as that of Example 4 was prepared. The cell suspension was passed through the system under the following conditions: flow rate into cell suspension inlet port: 420 mL/min (linear velocity: 366 cm/min); and initial filtrate flow rate from filtrate outlet port: 206 mL/min. The cell recovery rate and filtration time thus determined were 72% and 285 s, respectively.

Comparative Example 2

The same separation membranes as those used in Example 1 were used. The number of hollow fibers used was 600, and the prepared processing system had an inside membrane area of 0.25 m$^2$, and a total cross-sectional area of the hollow fiber separation membranes of 1.53 cm$^2$. The cell suspension was passed through the system under the following conditions: flow rate into cell suspension inlet port: 425 mL/min (linear velocity: 278 cm/min); and initial filtrate flow rate from filtrate outlet port: 278 mL/min. The cell recovery rate and filtration time thus determined were 64% and 285 s, respectively.

Example 5

A polyethersulfone hollow fiber separation membrane module [model: M2-M02E-100-F1N, inside membrane area: 0.105 m$^2$, hollow fiber inner diameter: 500 μm, pore size: 0.2 μm (from Spectrum Laboratories)] was evaluated in terms of cell concentration. The total cross-sectional area of the hollow fiber separation membranes as calculated from the actually measured effective length of the hollow fibers was 0.588 cm$^2$. The cell suspension was passed through the system under the following conditions: flow rate into cell suspension inlet port: 450 mL/min (linear velocity: 765 cm/min); and initial filtrate flow rate from filtrate outlet port: 269 mL/min. The cell recovery rate and filtration time thus determined were 83% and 235 s, respectively.

Example 6

The same hollow fiber module as that of Example 5 was used. The cell suspension was passed through the system under the following conditions: flow rate into cell suspension inlet port: 630 mL/min (linear velocity: 1071 cm/min); and initial filtrate flow rate from filtrate outlet port: 269 mL/min. The cell recovery rate and filtration time thus determined were 88% and 250 s, respectively.

Comparative Example 3

The same hollow fiber module as that of Example 5 was used. The cell suspension was passed through the system under the following conditions: flow rate into cell suspension inlet port: 450 mL/min (linear velocity: 765 cm/min); and initial filtrate flow rate from filtrate outlet port: 120 mL/min. The cell recovery rate and filtration time thus determined were 92% and 500 s, respectively.

Comparative Example 4

A polyethersulfone hollow fiber separation membrane module [model: M2-M02E-300-F1N, filtration area: 0.31 m$^2$, hollow fiber inner diameter: 500 μm, pore size: 0.2 μm (from Spectrum Laboratories)] was evaluated in terms of cell concentration. The total cross-sectional area of the hollow fiber separation membranes as calculated from the actually measured effective length of the hollow fibers was 1.737 cm$^2$. The cell suspension was passed through the system under the following conditions: flow rate into cell suspension inlet port: 520 mL/min (linear velocity: 299 cm/min); and initial filtrate flow rate from filtrate outlet port: 265 mL/min. The cell recovery rate and filtration time thus determined were 53% and 230 s, respectively.

Comparative Example 5

The same hollow fiber module as that of Comparative Example 4 was used. The cell suspension was passed through the system under the following conditions: flow rate into cell suspension inlet port: 1020 mL/min (linear velocity: 587 cm/min); and initial filtrate flow rate from filtrate outlet port: 566 mL/min. The cell recovery rate and filtration time thus determined were 72% and 106 s, respectively.

Example 7

Hollow fiber separation membranes made of a cellulose ester [model: M22M-100-01N, inside membrane area: 0.079 m², hollow fiber inner diameter: 600 µm, pore size: 0.2 µm (from Spectrum Laboratories)] were evaluated in terms of cell concentration. The total cross-sectional area of the hollow fiber separation membranes as calculated from the actually measured effective length of the hollow fibers was 0.531 cm². The cell suspension was passed through the system under the following conditions: flow rate into cell suspension inlet port: 440 mL/min (linear velocity: 829 cm/min); and initial filtrate flow rate from filtrate outlet port: 188 mL/min. The cell recovery rate and filtration time thus determined were 96% and 330 s, respectively.

Comparative Example 6

Hollow fiber separation membranes made of a cellulose ester [model: M22M-300-01N, inside membrane area: 0.25 m², hollow fiber inner diameter: 600 µm, pore size: 0.2 µm (from Spectrum Laboratories)] were evaluated in terms of cell concentration. The total cross-sectional area of the hollow fiber separation membranes as calculated from the actually measured effective length of the hollow fibers was 1.681 cm². The cell suspension was passed through the system under the following conditions: flow rate into cell suspension inlet port: 420 mL/min (linear velocity: 250 cm/min); and initial filtrate flow rate from filtrate outlet port: 222 mL/min. The cell recovery rate and filtration time thus determined were 45% and 275 s, respectively.

Comparative Example 7

Hollow fiber separation membranes made of a cellulose ester [model: M22M-301-01N, inside membrane area: 0.2 m², hollow fiber inner diameter: 1000 µm, pore size: 0.2 µm (from Spectrum Laboratories)] were evaluated in terms of cell concentration. The total cross-sectional area of the hollow fiber separation membranes as calculated from the actually measured effective length of the hollow fibers was 2.24 cm². The cell suspension was passed through the system under the following conditions: flow rate into cell suspension inlet port: 420 mL/min (linear velocity: 188 cm/min); and initial filtrate flow rate from filtrate outlet port: 200 mL/min. The cell recovery rate and filtration time thus determined were 36% and 300 s, respectively.

Example 8

Hollow fiber separation membrane made of polyethylene [trade name: SULFLUX FP02, inside membrane area: 0.2 m², hollow fiber inner diameter: 350 µm, pore size: 0.3 µm (from Kaneka Corporation)] were evaluated in terms of cell concentration. The total cross-sectional area of the hollow fiber separation membranes as calculated from the actually measured effective length of the hollow fibers was 1.206 cm². The cell suspension was passed through the system under the following conditions: flow rate into cell suspension inlet port: 710 mL/min (linear velocity: 589 cm/min); and initial filtrate flow rate from filtrate outlet port: 333 mL/min. The cell recovery rate and filtration time thus determined were 81% and 190 s, respectively.

Comparative Example 8

The same hollow fiber module as that of Example 8 was used. The cell suspension was passed through the system under the following conditions: flow rate into cell suspension inlet port: 415 mL/min (linear velocity: 344 cm/min); and initial filtrate flow rate from filtrate outlet port: 222 mL/min. The cell recovery rate and filtration time thus determined were 59% and 275 s, respectively.

TABLE 1

| | Ex.1 | Ex.2 | Ex.3 | Ex.4 | Com. Ex.1 | Com. Ex.2 | Ex.5 | Ex.6 | Com. Ex.3 | Com. Ex.4 | Com. Ex.5 |
|---|---|---|---|---|---|---|---|---|---|---|---|
| Hollow fiber material | Polyethersulfone (PES) | | | | | | Polyethersulfone (PES) | | | | |
| Inner diameter (µm) | | | 570 | | | | | | 500 | | |
| Pore size (µm) | | | 0.2 | | | | | | 0.2 | | |
| Inside membrane area(m²) | 0.1 | 0.12 | | 0.19 | | 0.25 | 0.105 | | | 0.31 | |
| Total cross-sectional area (cm²) | 0.637 | 0.765 | 0.765 | 1.147 | 1.147 | 1.53 | 0.588 | 0.588 | 0.588 | 1.737 | 1.737 |
| Linear velocity (cm/min) | 722 | 549 | 837 | 575 | 366 | 27.8 | 765 | 1071 | 765 | 299 | 587 |
| (Initial filtrate flow rate)/ (Flow rate) | 0.620 | 0.476 | 0.470 | 0.414 | 0.490 | 0.654 | 0.598 | 0.427 | 0.267 | 0.510 | 0.555 |
| Recovery rate (%) | 88 | 84 | 100 | 99 | 72 | 64 | 83 | 88 | 92 | 53 | 72 |
| Time (s) | 190 | 290 | 210 | 200 | 285 | 285 | 235 | 250 | 500 | 230 | 106 |

| | Ex.7 | Com. Ex.6 | Com. Ex.7 | Ex.8 | Com. Ex.8 |
|---|---|---|---|---|---|
| Hollow fiber material | Cellulose ester (ME) | | | Polyethylene (PE) | |
| Inner diameter (µm) | | 600 | 1000 | 350 | |

TABLE 1-continued

| | | | | | |
|---|---|---|---|---|---|
| Pore size (μm) | | | 0.2 | | 0.3 |
| Inside membrane area (m$^2$) | 0.079 | 0.25 | 0.2 | | 0.2 |
| Total cross-sectional area (cm$^2$) | 0.531 | 1.681 | 2.24 | 1.206 | 1.206 |
| Linear velocity (cm/min) | 829 | 250 | 188 | 589 | 344 |
| (Initial filtrate flow rate)/(Flow rate) | 0.427 | 0.529 | 0.476 | 0.469 | 0.535 |
| Recovery rate (%) | 96 | 45 | 36 | 81 | 59 |
| Time (s) | 330 | 275 | 300 | 190 | 275 |

As clearly seen in Table 1, cell concentrates can be prepared at high cell recovery rates by processing cell suspensions using a cell suspension processing system in which the hollow fiber separation membranes have a total cross-sectional area of 0.5 cm$^2$ to 1.5 cm$^2$, and an inside membrane area of 0.2 m$^2$ or less, under the conditions that the cell suspension is flowed inside the hollow fiber separation membranes at a linear velocity of 500 cm/min to 1200 cm/min, and the quotient of the division of the initial filtrate flow rate from the filtrate outlet port by the flow rate into the cell suspension inlet port is 0.4 to 0.7.

As described above, the production method of the present invention allows for efficient recovery of cells in a short time while removing unnecessary components other than cells, such as proteins, in suspensions, and allows cell concentrates to be prepared while reducing cell clogging in hollow fibers. Further, the production method of the present invention causes less damage to cells because washing and other processes that impose a burden on cells are not performed.

Cell concentrates prepared by the production method of the present invention can be used to provide even cells for use in cell therapy because the method can efficiently concentrate only target cells by aseptic operations, and the method does not use multiple hollow fibers and thus can prevent leakage of the materials, resulting in high safety.

REFERENCE SIGNS LIST

1. Tubular housing
2. Body
3. Head
4. Filtrate outlet port
5. Bundle of hollow fiber separation membranes
6. Open end (indicated by dots)
7. Resin layer (hatched area)
8a. Cell suspension inlet port
8b. Cell suspension outlet port
9. Header

The invention claimed is:

1. A method for producing a cell concentrate comprising filtration of a cell suspension using an inside-out filtration system, the system comprising:
   a cell suspension inlet port;
   a filtrate outlet port;
   a cell suspension outlet port; and
   a set of hollow fiber separation membranes provided between the cell suspension inlet port and the cell suspension outlet port,
   wherein
   the hollow fiber separation membranes have a total cross-sectional area of 0.5 cm$^2$ to 1.5 cm$^2$,
   the hollow fiber separation membranes have an inside membrane area of 0.2 m$^2$ or less,
   the cell suspension is flowed inside the hollow fiber separation membranes at a linear velocity of 500 cm/min to 1200 cm/min,
   the quotient of the division of an initial filtrate flow rate from the filtrate outlet port by a flow rate into the cell suspension inlet port is 0.4 to 0.7,
   a cell recovery rate is at least 81%, and
   a filtration time, measured from the start to the end of filtration of 1000 ml of the cell suspension, is 330 seconds or less.

2. The method for producing a cell concentrate according to claim 1, wherein the hollow fiber separation membranes have an inner diameter of 300 μm to 1000 μm.

3. The method for producing a cell concentrate according to claim 1, wherein the hollow fiber separation membranes have an average pore size of 0.1 μm or more.

4. The method for producing a cell concentrate according to claim 1, wherein the hollow fiber separation membranes are made of a polysulfone-, polyolefin-, or cellulose-based material.

5. The method for producing a cell concentrate according to claim 1,
   wherein the hollow fiber separation membranes are made of polyethersulfone.

6. The method for producing a cell concentrate according to claim 1,
   wherein the cell suspension is an immune cell suspension.

7. A method for producing a cell concentrate, comprising the steps of:
   washing a cell concentrate obtained by the production method according to claim 1 by repeating dilution with a liquid free from cells and concentration; and
   further concentrating the resulting concentrate.

8. A method for cryopreserving cells, comprising cryopreserving a cell concentrate obtained by the production method according to claim 1 with liquid nitrogen.

9. The method of claim 1, wherein the cell suspension is a human cell suspension.

10. The method of claim 9, wherein the human cell suspension is human immune cell suspension.

* * * * *